US012180128B2

(12) United States Patent
Banish et al.

(10) Patent No.: US 12,180,128 B2
(45) Date of Patent: Dec. 31, 2024

(54) CAPSAICINOID SMOKE

(71) Applicant: Michele Banish, Huntsville, AL (US)

(72) Inventors: R Michael Banish, Huntsville, AL (US); Peter S Erbach, Huntsville, AL (US); Joseph Foster, Las Cruces, NM (US)

(73) Assignee: Michele Banish, Huntsville, AL (US)

( * ) Notice: Subject to any disclaimer, the term of this patent is extended or adjusted under 35 U.S.C. 154(b) by 224 days.

(21) Appl. No.: 17/162,412

(22) Filed: Jan. 29, 2021

(65) Prior Publication Data

US 2021/0147313 A1 May 20, 2021

Related U.S. Application Data

(63) Continuation of application No. 15/482,481, filed on Apr. 7, 2017, now Pat. No. 10,941,086, which is a (Continued)

(51) Int. Cl.
*C06D 3/00* (2006.01)
*A61K 9/00* (2006.01)

(Continued)

(52) U.S. Cl.
CPC ................ *C06D 3/00* (2013.01); *A61K 9/007* (2013.01); *A61K 31/165* (2013.01); *A61K 47/02* (2013.01);

(Continued)

(58) Field of Classification Search
None
See application file for complete search history.

(56) References Cited

U.S. PATENT DOCUMENTS 1,886,394 A * 11/1932 Goss ........................ C06D 3/00 424/40
2,294,415 A * 9/1942 Mcbride ................ F42B 12/50 102/368

(Continued)

FOREIGN PATENT DOCUMENTS

CN 111 011 380 A 4/2020
DE 20 2004 021 107 U1 10/2006

(Continued)

OTHER PUBLICATIONS

"Glycerol propoxylate (1PO/OH) triacryiate—Safety Data Sheet" SiGMA-ALDRiCH Corporation; Version 5.5; revision date May 24, 2016; print date Apr. 26, 2019, pp. 1-7.

(Continued)

*Primary Examiner* — Aileen B Felton
(74) *Attorney, Agent, or Firm* — Nicholas J. Landau; Maynard Nexsen PC

(57) ABSTRACT

A smoke producing method and device of the present disclosure produces a non-incendiary, organic-polymerization based, smoke-producing reaction. Some versions of the smoke are effective carriers for capsaicinoid compounds. The method of generating smoke comprises initiating a frontal polymerization reaction by heating a composition comprising a monomer compound that exothermically polymerizes upon initiation with an initiator compound and an initiator compound that initiates polymerization of the monomer compound present at a mass concentration that is at least five percent of the mass concentration of the monomer compound. The polymerization of the monomer compound is exothermic, and in one embodiment the concentration of initiator compound is at least five percent of the concentration of monomer compound. The smoke mainly (Continued)

comprises thermal decomposition products of the initiator compound.

13 Claims, 10 Drawing Sheets

Related U.S. Application Data continuation-in-part of application No. 13/889,218, filed on May 7, 2013, now Pat. No. 9,617,195.

(60) Provisional application No. 61/643,565, filed on May 7, 2012.

(51) Int. Cl.

| | |
|---|---|
| ***A61K 31/165*** | (2006.01) |
| ***A61K 47/02*** | (2006.01) |
| ***A61K 47/14*** | (2017.01) |
| ***C06D 7/00*** | (2006.01) |
| ***F24V 30/00*** | (2018.01) |
| ***F41H 9/06*** | (2006.01) |
| ***F42B 12/48*** | (2006.01) |

(52) U.S. Cl.

CPC ................ *A61K 47/14* (2013.01); *C06D 7/00* (2013.01); *F41H 9/06* (2013.01); *F42B 12/48* (2013.01); *F24V 30/00* (2018.05)

(56) References Cited

U.S. PATENT DOCUMENTS

| | | | |
|---|---|---|---|
| 2,482,877 | A | 9/1949 | Schmerling |
| 2,769,849 | A | 11/1956 | Schmerling |
| 2,995,526 | A | 8/1961 | Ment |
| 3,036,939 | A | 5/1962 | Camp |
| 3,625,855 | A | 12/1971 | Douda |
| 3,668,243 | A | 6/1972 | Quinn |
| 3,811,968 | A | 5/1974 | Sayles |
| 3,881,420 | A | 5/1975 | Smith et al. |
| 3,960,087 | A | 6/1976 | Beatty et al. |
| 4,366,010 | A | 12/1982 | Sedat |
| 4,455,252 | A | 6/1984 | Wylegala et al. |
| 4,483,537 | A | 11/1984 | Hanada et al. |
| 4,499,240 | A | 2/1985 | Valentine |
| 4,607,060 | A | 8/1986 | Kmiec et al. |
| 4,692,497 | A | 9/1987 | Gendreau et al. |
| 4,697,521 | A | 10/1987 | Espagnacq et al. |
| 4,841,865 | A | 6/1989 | Liberman |
| 5,098,488 | A | 3/1992 | Hassell et al. |
| 5,154,782 | A | 10/1992 | Shaw et al. |
| 5,340,395 | A | 8/1994 | Larmignat et al. |
| 5,656,794 | A | 8/1997 | Krone et al. |
| 5,679,722 | A | 10/1997 | Tamura |
| 5,744,534 | A | 4/1998 | Ishiharada et al. |
| 6,017,586 | A | 1/2000 | Payn et al. |
| 6,242,521 | B1 | 6/2001 | Hwang |
| 6,300,457 | B1 | 10/2001 | Rubin et al. |
| 6,412,416 | B1 | 7/2002 | Rouse et al. |
| 6,558,487 | B1 | 5/2003 | Tadros |
| 6,666,143 | B1 | 12/2003 | Collins |
| 7,699,004 | B2 | 4/2010 | Muro |
| 7,946,228 | B2 | 5/2011 | Dindl et al. |
| 7,975,615 | B1 | 7/2011 | Apple |
| 9,617,195 | B2 | 4/2017 | Erbach et al. |
| 10,941,086 | B2 | 3/2021 | Banish et al. |
| 2001/0018880 | A1 | 9/2001 | Pfeil et al. |
| 2002/0037960 | A1 | 3/2002 | Kovar et al. |
| 2002/0132885 | A1 | 9/2002 | Burns et al. |
| 2003/0114622 | A1 | 6/2003 | Masawaki |
| 2003/0215588 | A1 | 11/2003 | Yeager et al. |
| 2006/0147725 | A1 | 7/2006 | Gust et al. |
| 2008/0199618 | A1 | 8/2008 | Wen et al. |
| 2009/0155485 | A1 | 6/2009 | Hoyle et al. |
| 2012/0052281 | A1 | 3/2012 | Ishiguro et al. |
| 2012/0055075 | A1 | 3/2012 | Winkler et al. |
| 2012/0267016 | A1* | 10/2012 | Lombardi ............... C06B 29/08 149/75 |
| 2013/0172482 | A1* | 7/2013 | Allen ................. C08G 64/0291 524/599 |
| 2021/0179509 | A1 | 6/2021 | Banish et al. |

FOREIGN PATENT DOCUMENTS

| | | | |
|---|---|---|---|
| DE | 20 2010 009 717 | U1 | 10/2010 |
| ES | 2302620 | A1 | 7/2008 |
| FR | 3 018 277 | A1 | 9/2015 |
| JP | S59-159809 | A | 9/1984 |
| JP | 2634849 | B2 | 7/1997 |
| JP | 2000-07478 | A | 1/2000 |
| JP | 2000-44691 | A | 2/2000 |
| JP | 2007-161500 | A | 6/2007 |
| JP | 2016-069368 | A | 5/2016 |
| KR | 10-2002-0048605 | A | 6/2002 |
| KR | 10-2012-0140383 | A | 12/2012 |
| WO | 2006/076033 | A1 | 7/2006 |
| WO | 2013/169813 | A2 | 11/2013 |
| WO | 2018/187809 | A1 | 10/2018 |

OTHER PUBLICATIONS

"US EPA—Pesticides—R.E.D. Fact Sheet for Thymol", Office of Prevention, Pesticides and Toxic Substances, (H-7508W), EPA-738-F-93-010, Sep. 1993, pp. 1-199.

Product Data Sheet. Trigonox 29-408-gr. 1, 1-Di(tert-butylperoxy)-3,3,5-trimethyl cyclohexane granules calcium carbonate and silica. AkzoNobel. Apr. 2010, pp. 2.

Binici, B., et al., "Spherically Propagating Thermal Polymerization Fronts", Journal of Polymer Science: Part A: Polymer Chemistry, vol. 44, Nov. 20, 2005, pp. 1387-1395 (2006).

Capsaicin/C 18H27NO3—PubChem; web-page available at https://pubchern.ncbi.nlrn.nih.gov/cornpound/Capsaicin; pulled from world wide web on Sep. 3, 2019; pp. 1-68.

Charles, Nason et al., "UV Induced Frontal Polymerization of (Meth)Acrylates", ©RadTech e|5 2004 Technical Proceedings, Apr. 12, 2004, pp. 1-8.

Marini E. et al., "Antimicrobial and Anti-Virulence Activity of Capsaicin Against Erythromycin-Resistant, Cell-Invasive Group A Streptococci", Frontiers in Microbiology, vol. 6, Article 1281, Nov. 13, 2015, pp. 1-7.

Masere, J. et al., "Period-Doubling Behavior in Frontal Polymerization of Multifunctional Acrylates", Choas, vol. 9, Issue 2, 1999, pp. 315-322.

Pojman, J.A., "Frontal Polymerization" In: Matyjaszewski Kand Moller M. (eds), Polymer Science: A Comprehensive Reference, vol. 4, 2012, pp. 957-980.

Pojman, J.A., "Photoinitiated Frontal Polymerization for Rapid Repair and for Studying Sperically Propagating Thermal Fronts", ©RadTech e|5 2006 Technical Proceedings, Apr. 6, 2006, pp. 8.

Pojman, J.A., et al., "Snell's Law of Refraction Observed in Thermal Frontal Polymerization" Chaos, vol. 17, No. 3, Sep. 1, 2007, pp. 9.

Scoville, W.L., "Note on Capsicums", The Journal of the American Pharmaceutical Association, vol. 1, 1912, pp. 453-454.

Viner, V.G. et al., "The effect of phase change materials on the frontal polymerization of a triacrylate", Physica D: Nonlinear Phenomena, vol. 239, Issue 11, Jun. 1, 2010, pp. 838-847.

Washington, R.P., et al., "Frontal Free-Radical Polymerization: Applications to Materials Synthesis", Polymer News 2003, Copyright © 2003 Taylor & Francis, Inc., vol. 28, No. 10, 2003, pp. 303-310.

Xia, W.Z. et al., "Exotherm control in the thermal polymerization of nona-ethylene glycol dimethacrylate (NEGDM) using a dual radical initiator system", Polymer 44, Copyright © 2002 Published by Elsevier Science Ltd, vol. 44, No. 1, Nov. 22, 2002, pp. 79-88.

International Search Report and Written Opinion issued Dec. 16, 2013, in International Patent Application No. PCT/US2013/03994, filed May 7, 2013, 14 Pages.

(56) References Cited

OTHER PUBLICATIONS

Extended European Search Report and Opinion mailed on Dec. 1, 2015, in European Patent Application No. 13788459.9, filed on May 7, 2013, 11 Pages.
Office Action mailed on Aug. 22, 2016, in European Patent Application No. 13788459.9, filed on May 7, 2013, 3 Pages.
International Search Report and Written Opinion mailed on Jul. 26, 2018, in International Patent Application No. PCT/US2018/026731, filed on Apr. 9, 2018, 8 Pages.
Examination Report No. 1 mailed on May 11, 2021, in Australian Patent Application No. 2018249955, filed on Apr. 9, 2018, 2 Pages.
Written Opinion mailed on Sep. 22, 2021, in International Patent Application No. PCT/US2021/033554, filed on May 21, 2021, 7 Pages.
Cheng, S-Y. et al., "Runaway reaction on tert-butyl peroxybenzoate by DSC tests", Journal of Thermal Analysis and Calorimetry, Kluwer Academic Publishers NL, vol. 93, Issue 1, Jul. 1, 2008, pp. 121-126 (Abstract).
Tseng, J-M et al., "Evaluation of a tert-Butyl Peroxybenzoate Runaway Reaction by Five Kinetic Models", Industrial and Engineering Chemistry Research, American Chemical Society, vol. 50, No. 8, Apr. 20, 2011, pp. 4783-4787 (Abstract).
Viner V., et al., "Effect of Filler Choice on a Binary Frontal Polymerization System", Journal of Physical Chemistry B, American Chemical Society, vol. 115, No. 21, Jun. 2, 2011, pp. 6862-6867 (Abstract).
Viner V., et al., "Effects of thiols, lithium chloride, and ethoxylated monomers on the frontal polymerization of a triacrylate", Journal of Polymer Science, Part A: Polymer Chemistry, John Wiley and Sons Inc., vol. 49, No. 21, Nov. 1, 2011, pp. 4556-4561 (Abstract).

* cited by examiner

CAPSAICINOID SMOKE

CROSS-REFERENCE TO RELATED APPLICATIONS

This application is a continuation of U.S. patent application Ser. No. 15/482,481 filed 7 Apr. 2017 (pending); which is a continuation-in-part of U.S. Pat. No. 9,617,195, filed 7 May 2013 (issued); which cites the benefit of U.S. Pat. App. No. 61/643,565, filed 7 May 2012.

BACKGROUND

Smoke generation devices generate smoke in military applications for signaling, for marking target or landing zones, and for screening of movements. Devices for producing obscurant smoke for the battlefield are typically either explosively-charged, meaning the devices use an explosive charge to disperse fine particles, or chemically-reactive, meaning a chemical reaction generates smoke. Some chemically-reactive smoke generation devices utilize inorganic materials that are activated in a self-sustaining chemical reaction to produces smoke as a byproduct of the heat generation. Examples of these smoke generation devices are thermite grenades and the HC (hexachloroethane), TA (terephthalic acid), and WP (white phosphorus, or red phosphorus) smoke grenades in the current military inventory. The reactions in these devices have large free energies of reaction, and are by necessity exothermic. As such, the reactions produce considerable heat and toxic, or hazardous, compounds. Typical smoke-producing reactions produce much more heat than is necessary to sustain the reaction. The adiabatic flame temperatures of these materials greatly exceed 1000° C., which is one of the factors that leads to their incendiary characteristics.

Heat generation is an issue with either explosively-charged or chemically-reactive smoke generation devices. Traditional smoke generation devices are incendiary and can set cloth, fuel, ammunition and other combustibles on fire, and cause serious burns or death. What is desired is a smoke producing mixture that is capable of producing smoke while minimizing the incendiary and chemical hazards of present devices.

Capsaicinoids are a class of compounds first discovered in the fruits of genus *Capsicum* (chili peppers). Capsaicinoids have the unusual property of causing sensory irritation in mammals, including humans, and produce a sensation of burning in any tissue with they contact. The burning sensation can be very severe, causing excruciating pain, fainting, and even temporary blindness. However, capsaicinoids have very low toxicity, and while contact with the compounds can be agonizingly painful, exposure has few or no lasting effects. These properties would seem to make capsaicinoids ideal nonlethal weapons. However, delivery of capsaicinoids is difficult. Capsaicinoids are non-volatile and extremely insoluble in water. There have been no successful efforts to deliver capsaicinoids as a gas or smoke, due to their low volatility and insolubility. As a result, the use of capsaicinoids as nonlethal weapons has been limited to delivery by sprays, which have many disadvantages. Sprays are inaccurate, and even if the target is hit, the target will not feel the full effects of the capsaicinoids unless the spray contacts the target's mouth, nose, or eyes. Sprays have limited range, giving the user little time to aim and allowing the target to achieve close proximity to the user before the user has a chance to use the spray. This disadvantage is especially acute when the user is targeting an attacking animal, many of which can cover the distance between the maximum range of the spray and the user within one or two seconds.

Consequently there is a need in the art for a means to deliver capsaicinoids in the form of a smoke, ideally a non-toxic and non-pyrotechnic smoke that will neither poison nor burn those exposed to it.

SUMMARY

A smoke producing method and device of the present disclosure produces a non-incendiary, organic-polymerization based, smoke-producing reaction. Some embodiments of the smoke contain one or more capsaicinoid compounds. In one embodiment, the method of generating smoke comprises initiating a frontal polymerization reaction by heating a composition comprising a monomer compound that exothermically polymerizes upon initiation with an initiator compound, and an initiator compound that initiates polymerization of the monomer compound present at a mass concentration that is at least five percent (5%) of the mass concentration of the monomer compound. In this embodiment, the smoke produced mainly comprises thermal decomposition products of the initiator compound. The initiator may also decompose exothermically. The by-product that results from smoke generation in this embodiment is a solid material that will slowly degrade over time if exposed to outside conditions.

In a typical polymer reaction, the initiator concentration controls the chain length of the produced polymer. Also, in a typical polymer reaction, the initiator is consumed, chemically bonded to the polymeric molecules. In this type of smoke producing reaction the objective, at a minimum, is to decompose and volatilize initiator as well as additives and/or portions of the monomer itself.

Frontal polymerization (FP) is a process in which the reaction propagates directionally through the reaction vessel because of the coupling of thermal transport and the Arrhenius-dependence of the kinetics of an exothermic reaction. Frontal polymerization is very much like a flame but propagating through condensed materials instead of a gas. In frontal polymerization reactions, the components are premixed, but stable until initiated by an external source. For example, consider a 2-part epoxy: as soon as the two components are mixed, an exothermic reaction is initiated). As another example, RTV type polymers will self-initiate once exposed to oxygen. The reactions developed here operate differently than either of these or similar types of examples.

Frontal Polymerization is a form of self-propagating high-temperature synthesis (SPHTS). Here the term "high-temperature" is used to indicate higher than ambient temperature, but certainly lower in temperature than pyrotechnic igniters used in current smoke grenades. In FP as in the case of SPHTS the system will not start reacting until sufficient energy is applied to the material to get a reaction front propagating through the system. This self-propagating wave moves rapidly through the system as long as sufficient heat is generated at the propagation front. Thus, these systems are inherently stable until a sufficient amount of energy is added to start the reaction. Materials with high heat capacity can be incorporated into the mixture. Thus, the system can be turned such that the heat released does not lead to excessive heating of the surrounding environment, thereby reducing incendiary hazards. In other words, the addition of filler materials has the effect of reducing the front temperature and thereby reducing the incendiary hazard since the "excess"

heat generated can be "absorbed" in the material itself and not transmitted to the environment.

The reactants used in the smoke producing compounds disclosed herein have reaction temperatures in the range of 300-400° C. (However, as indicated above, the reaction temperature may be tuned to above ambient to 400° C.). Thus, even with combustible, low heat capacity materials it is difficult for a device using these materials, particularly the exposed, exterior, material to get above the temperatures necessary to cause structural materials, such as wood, to combust. It is also unlikely that if there were an accidental activation of a device during storage that other devices in the same container would ignite or that other storage containers would be breached. In addition, the manufacture of devices with lower energetic materials is also much less hazardous that current pyrotechnic based devices.

In a typical polymerization compound to make a polymer, the initiator concentrations are on the order of 1% or less by mass. This concentration is expressed in polymer literature as 1 pph (parts per hundred of the monomer). As an example, a 10 gram sample with 20 pph initiator and 10 pph fumed silica contains 10 grams of monomer, 2.0 grams of initiator, and 1.0 grams of fumed silica. In experimental testing of the smoke producing compound of the present disclosure, it was found that increasing the amount of initiator in the compound increased the amount of smoke produced.

Smoke production is caused by a decomposition of the monomer-initiator pair in the smoke generation compound. The fact that smoke production comes from the monomer-initiator pairs has advantages. First, lower reaction temperatures can be used because higher temperatures are not required to volatize a third component in the mixture. Since the initiator is the source of the smoke in this embodiment, it is only necessary to have a sufficient reaction temperature to sustain the initiator decomposition reaction. Also, a higher efficiency of smoke production can be achieved. Since the smoke is due to the initiator and no longer to a third component the "extra" mass was no longer necessary. The monomer itself may decompose, leading to additional smoke production.

In a first aspect, a composition for the non-pyrotechnic generation of capsaicinoid-containing smoke is provided, the composition comprising: a monomer compound that exothermically polymerizes upon initiation with an initiator compound; an initiator compound that initiates polymerization of the monomer compound, said initiator present at a mass concentration that is at least double the mass concentration of the monomer compound; and a capsaicinoid compound in an amount effective to produce an organoleptic effect in the smoke.

In a second aspect, a method of generating capsaicinoid-containing smoke is provided, the method comprising initiating a frontal polymerization reaction by heating the composition above to a sufficient temperature, and generating smoke comprising the capsaicinoid and thermal decomposition products of the initiator compound.

In a third aspect a non-pyrotechnic capsaicinoid smoke generator is provided, said smoke generator comprising: a support member having a length and a width; the composition above supported by the support member; an ignition wire in contact with the composition; and a source of electric current connected to the ignition wire.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

The disclosure can be better understood with reference to the following drawings. The elements of the drawings are not necessarily to scale, emphasis instead being placed upon clearly illustrating the principles of the disclosure. Furthermore, like reference numerals designate corresponding parts throughout the several views.

DETAILED DESCRIPTION

Figure 1:
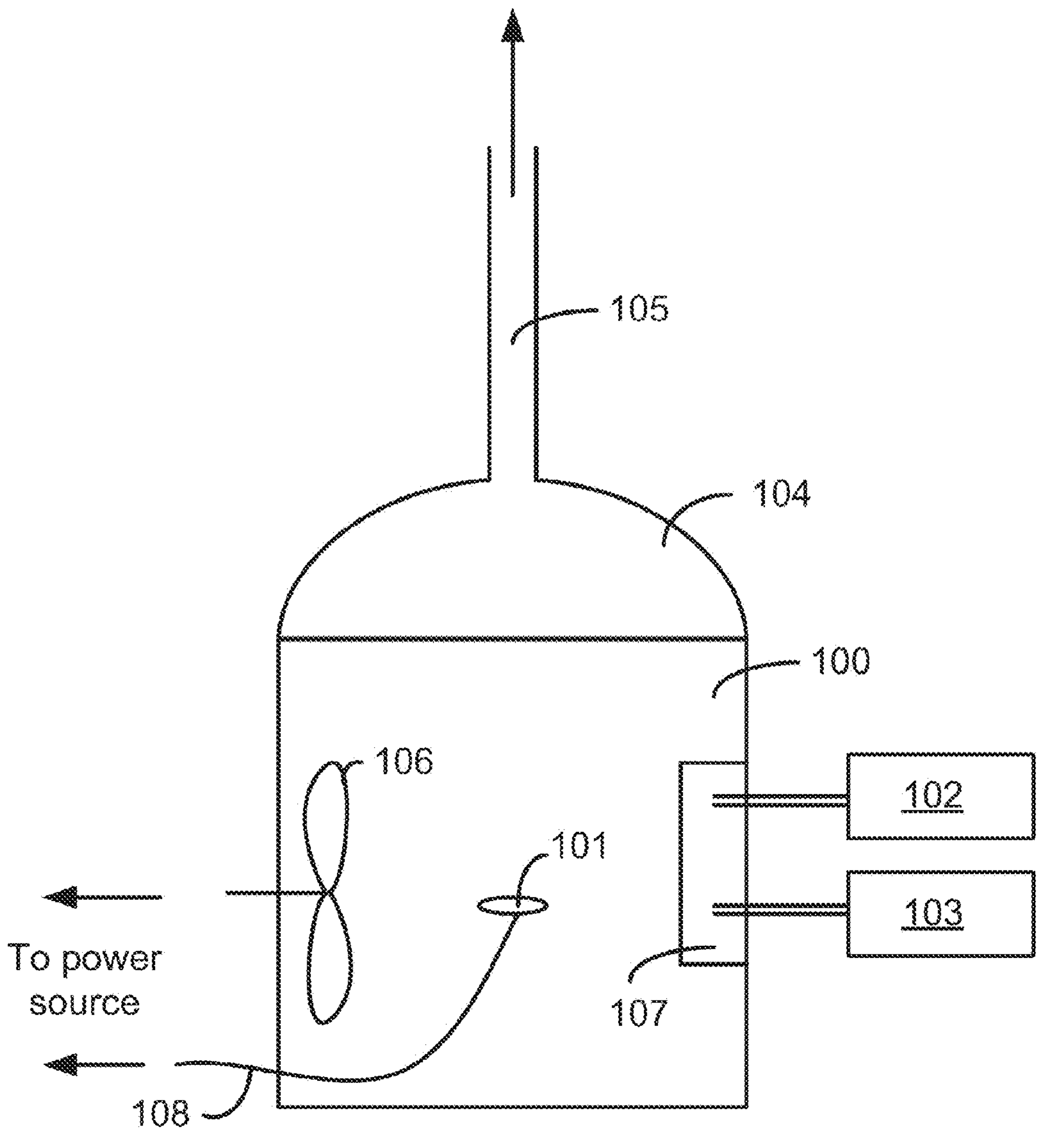
FIG. 1 is a functional schematic of an exemplary test performed to measure the characteristics of a smoke producing sample.

The disclosure provides compositions for producing smoke. The smoke may contain one or more capsaicinoid compounds. Various embodiments of the compositions disclosed herein have advantages over previously known smoke-producing compositions; for example: low or no flame front (safe to use indoors, outdoors, and in training environments with flame hazards); low toxicity of the smoke and any non-smoke residues; environmentally friendly (little to no residue or hazardous byproducts); high packing density; high smoke yield/low agglomeration of smoke particles; easily aerosolized, rapid smoke generation (short time constant); good obscuration properties in the visible portion of the electromagnetic spectrum; long smoke durations with appropriate buoyancy; and good shelf life (i.e., after mixing components, the mixture does not self-initiate polymerization).

In general, there are a minimum of two components—a monomer and an initiator—required to achieve polymerization. In the present embodiment, the monomer provides the carbon compounds that will form the polymer chains and the initiator provides a mechanism to join the carbon compounds together. The baseline monomer used in the composition of the present disclosure is TMPTA (trimethylolpropane triacrylate). Other monomers are possible and it is possible to combine other materials with the monomer for various effects. For example, by combining TMPTA with dibutyl phthalate, a large amount of smoke can be generated, but the smoke is not as buoyant as with TMPTA only. It may be possible to develop a smoke with tailorable buoyancy—which is useful if it is desired to reduce the duration of the smoke. Currently, in an enclosed environment, the smoke producing compound of the present disclosure can result in smoke durations in excess of 20 min. Note that the monomer may also be a material with a backbone other than carbon; for example, the Silicon backbone in Silicone caulk or RTV sealant. In addition, the production of a polymer is not a necessity. The primary role of the monomer is that it provides the heat source so that the reaction proceeds in a timely manner. In Frontal Polymerization, as opposed to other polymerization mechanisms, the mixed monomer and initiator are stable until an external excitation source is added.

For example, by combining TMPTA with methyl benzoate, benzyl benzoate, and pentyl acetate, considerable amounts of smoke are produced but they have slightly less buoyancy than TMPTA only. This may result in the ability to tailor the buoyancy. These materials are esters used as food additives/aromatics. An additional reason for employing TMPTA monomer in the smoke mixture is that it is a good, high quality (purity), inexpensive monomer.

The baseline initiator for the smoke producing compound of the present disclosure is Luperox®-231 (1,1-Bis(tert-butylperoxy)-3,3,5-trimethylcyclohexane). Other initiators are possible but may have, or are shown to have, undesirable effects. For example, t-butyl peroxybenzoate may be used with good smoke generation results. However, the benzoic acid byproducts are considerably more hazardous than the trimethyl cyclohexanes (TMCH) generated with the baseline initiator. The trimethyl cyclohexane smoke product or byproduct is not an acid or acid forming material. According to the toxicity analysis the inhalation and LD50 thresholds of TMCH are much higher than for the currently used materials (HC and RP).

One embodiment of the smoke producing compound of the present disclosure requires two other components: an ignition mechanism and a filler. The ignition (or initiation) mechanism used in the testing disclosed herein was a heat source. The heat source does not have to, but can, be pyrogenic. To date, Estes model rocket igniters, simple nichrome wire loops attached to voltage sources, hot air from a heat gun, soldering iron tips, open flame, focused intense light, have all been used to initiate the FP reaction. This ignition mechanism list is not exhaustive. Other ignition mechanisms considered are: piezo devices that might be used to ignite something more pyrogenic such as cannon fuse, battery powered voltage sources for nichrome wire, etc. A mixture including monomer and initiator will not self-initiate without an ignition source—this contributes to the long shelf life and inertness of the material.

Ignition tests have been conducted with a 1" conduction loop of 30 gauge nickel-chromium (NiCr, or nichrome) wire with a resistance/unit length of approximately 0.5 Ohm/in. The wire was buried slightly under the surface of the smoke producing composition (which is typically in gel form) and a current draw of approximately 1 Amp was sufficient to initiate the FP reaction. Using Power, $P=I^2R$, where I is the current in Amps and R is the resistance in Ohms, this yields an input Power of $P=(1\ Amp)^2(0.5\ Ohm)=0.5\ W$.

In the current embodiment (for an application such as smoke grenade usage), the filler provides a mechanism, or a matrix, for the smoke mixture to have a shape other than that provided by its container (e.g., a liquid or gas assumes the shape of its container, but a solid or a gel may not). Fumed silica, kaolin (clay) powder, and powdered sugar have all been used as fillers. Fumed silica has provided the best performance—the mass required is low, it has a high area-mass ratio which provides significant thickening with a low thermal mass. This prevents it from robbing the reaction of the heat required for the reaction to propagate. Increasing the amounts of kaolin powder and powdered sugar have been shown to rob the reaction of its necessary heat and reduce the amount of smoke.

There are other envisioned applications where the smoke mixture is left as a liquid—so the filler/thickening agent might not be required or might be detrimental to the application. An example of a situation in which the thickening agent is not required: A liquid smoke mixture is carried on a military robot. If an individual approached too close to the robot, the liquid would be sprayed onto a hot surface (i.e., hot plate or wire) located somewhere on the robot. This would generate a signaling/deterrent smoke. In addition, this might not require large temperatures to initiate the reaction so that the smoke generation mechanism is not an incendiary hazard to the robot or to the local environment.

The primary mixture components of the smoke producing composition also have enough thermal conductivity that, if a point ignition source is applied, the bulk mixture reactants may quickly convect the required reaction energy away from the reaction site and cause the reaction to quench itself. The very low thermal conductivity of fumed silica "insulates" the reaction region, preventing the heat of reaction or of initiation from convecting away too rapidly. When no filler is present a large area heat source, such as a heat gun, may be required to inject significant heat into the mixture to overwhelm the convective heat losses. Present experimentation has shown cases where, for all other mixture components held constant, increases in filler (fumed silica) have resulted in a higher absorption smoke. The filler may provide more nucleation sites for polymerization to initiate.

In one embodiment of the smoke producing compound, if ×g of TMPTA monomer is used, then greater than 0.1×g of Luperox® 231 initiator, and greater than or equal to 0.1×g of fumed silica filler are to be used. This mixture would be considered a "greater than 10 pph" mixture (greater than 10 parts initiator to 100 parts monomer). Note that the initiator concentration may be allowed to approach infinity (i.e., no monomer) and still generate smoke. The initiator may also decompose exothermically. In comparison, ratios for standard reactions wherein the polymerization product, not the smoke product, is desired, are characterized by initiator concentrations utilizing much less than 10 pph—typically 0.01 pph-0.1 pph, but less than 1 pph.

The TMPTA (trimethylolpropane triacrylate) is a trifunctional monomer. This means that there are three double-bond carbon ends associated with each monomer molecule. Typical monomer-polymer system include compounds that have a single carbon double-bond along the monomer chain; ethylene, styrene, vinyl chloride. A single initiator molecule causes the breaking of the double bond and a monomer free radial to be formed. This monomer free radical then reacts with other monomers and a polymer molecule begins to grow. Termination of the process occurs when two free radicals combine; either a second polymer free radical or the other half of the initiator molecule. Polymer molecules of 1000 to 100,000 monomers are commonly produced. One of the controlling parameters of the final chain length is the number of initiator molecules added. Thus, typical initiator concentrations are a few hundredths to millionths of percent; high initiator concentrations yield low molecular weight polymer molecules. The heat generated from the polymerization process is due to the breaking of the carbon double bond and the formation of a carbon single bond. This process releases 60 kJ of energy per mole of double bonds. The process temperature of the reaction depends on the heat capacity of the monomer molecules. Molecules such as poly(ethylene) C2H4 have a much lower heat capacity than molecules such as styrene C8H10 and have much higher reaction temperature since they both have a single double-bonded carbon that participates in the reaction.

Capsaicinoids are a class of compounds originally discovered in *Capsicum* spp., although synthetic derivatives have also been produced. Capsaicinoids are generally related to capsaicin, which has the following structure:

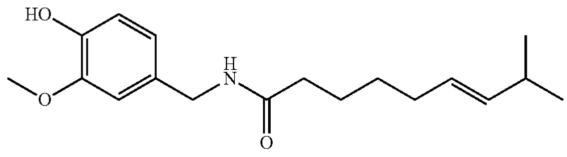

Capsaicin

Capsaicinoids tend to share the 4-hydroxy-3-methoxyphenyl methyl group but vary in the structure of the hydrocarbon tail bound to the amide moiety. For example, some capsaicinoids lack double bonds in the hydrocarbon tail, others lack the pendant methyl group, other vary the location of the unsaturated carbons, in still others the length of the hydrocarbon tail varies from about 7 to about 9 carbons (not counting pendant groups). Loosely defined, a capsaicinoid is any ester of vanillamine having a hydrocarbon tail at least 5 carbons in length.

The capsaicinoid is one that is exerts an organoleptic effect on the intended target (which will be a mammal). In this context "organoleptic" means producing a sensible effect, such as a burning sensation. The effect may be an irritant effect, meaning an effect that is at least painful. The irritant effect may also be one or more of ocular redness, ocular pain, lacrimation, blepharospasm, blindness, respiratory tract irritation, mucous membrane irritation, coughing, wheezing, intranasal pain, throat pain, laryngitis, headache, nausea, vomiting, runny nose, and shortness of breath.

Examples of capsaicinoids known to exert organoleptic or irritating effects include capsaicin, dihydrocapsaicin, nordihydrocapsaicin, homocapsaicin, homodihydrocapsaicin, and nonivamide. Salts, esters, and other derivatives of the capsaicinoid may be used, so long as the derivative has the desired organoleptic or irritant properties. The organoleptic properties of capsaicinoids (and other substances) are generally measured in the art by the method of Scoville (1912) *J. Am. Pharm. Assoc.* vol. 1, pp. 453-454 (incorporated by reference to teach this method). The method involves extracting one grain (64.8 mg) of the sample in 100 mL of ethanol; then serially diluting the extract in water. The serial dilutions are tasted by a panel of tasters, until the highest dilution in which the substance can be tasted is identified. The ratio of water to the ethanol extract in said highest tasteable dilution is the potency of the sample in "Scoville Heat Units" (SHU). In any instance in which a value or range of SHU is claimed, such value or range is based on the method of Scoville (1912). Various capsaicinoids have been assigned standard SHU values, as follows (a commonly eaten variety of *Capsicum annuum* has been included for reference):

TABLE 1

EXEMPLAR CAPSAICINOIDS AND THEIR SHU VALUES

| Compound | SHU |
|---|---|
| Capsaicin | $1.6 \times 10^7$ |
| Dihydrocapsaicin | $1.5 \times 10^7$ |
| Nonivamide | $9.1 \times 10^6$ |
| Nordihydrocapsaicin | $9.1 \times 10^6$ |
| Homodihydrocapsaicin | $8.6 \times 10^6$ |
| Homocapsaicin | $8.6 \times 10^6$ |
| Jalapeno pepper | $5\text{-}20 \times 10^3$ |

Any of the above capsaicinoids may be used. The concentration of capsaicinoid will be sufficient to confer an organoleptic property to the smoke, such as an irritant property. For example, some embodiments of the composition contain at least 1% w/w of the capsaicinoid. Further embodiments of the composition contain the capsaicinoid at 1-20% w/w, 2-15% w/w, or 5-10% w/w. Specific embodiments of the composition contain 5 or 10% capsaicinoid by weight.

The concentration of the capsaicinoid in the composition may also be designed to achieve a target SHU or SHU range. For example, some embodiments of the composition are at least $10^5$, $1.6\times10^5$, or $10^6$ SHU. Further embodiments of the composition contain the capsaicinoid at $1.6\times10^5$ to $3.2\times10^6$, $3.2\times10^5$ to $2.4\times10^6$, or $8\times10^6$ to $1.6\times10^7$ SHU. Specific embodiments of the composition are $8\times10^6$ or $1.6\times10^7$ SHU.

Experimental Testing

The addition of "excess" initiator, in this case Luperox® 231 (1,1-Di-(tert-butylperoxy)-3,3,5-trimethylcyclohexane)), to a trifunctional monomer is against all polymerization practice because it increases the amount of smoke and decreases the quality of the resultant polymer. In fact, the more initiator is added, the poorer the strength of the resultant polymer, because there are more voids, more fractures, etc. During the course of this work it was not clear, until experimental tests were performed, that the polymerization reaction would even occur as increasing amount of initiator were added to the monomer. Increasing the initiator amount beyond the minimum necessary to sustain the polymerization reaction, likely causes an excessive number of polymerization reactions to occur simultaneously in a confined space. The distinct polymers formed by these multiple polymerization reactions will not necessarily bond with other polymers to form longer polymers. The result is that shorter than normally desired polymer chains are formed, resulting in a far weaker polymer product. As the initiator concentration is increased excessively, the polymer product has much shorter chains and is far weaker.

A series of preliminary experiments were conducted with initiator concentrations from 1 to 15 pph (parts per hundred of monomer). These preliminary tests qualitatively indicated that higher initiator concentrations resulted in increasing smoke yields. More importantly, these tests indicated that high initiator concentrations did not adversely affect the rate of the polymerization process and that sufficient heat was generated for the initiator to decompose into a visible smoke.

FIG. 1 is a functional schematic of an exemplary test performed to measure the characteristics of a smoke producing sample 101 in a chamber 100. The chamber 100 was substantially one (1) cubic foot in volume (11"×12" by 10"). Specifically, a Fisher Scientific® Dry Box was used as an air tight chamber 100 in this test. An FP reaction of the sample 101 was remotely initiated via a wire 108 extending through the chamber wall and to a power source (not shown). A fan 106 inside the chamber 100 circulated the smoke (not shown) produced by the reaction. Visible spectra measurements were taken with an Ocean Optics HR2000 UV-Vis spectrometer 102. The optical cell (not shown) was a Starna 34-SOG-100 10 cm cell. Infrared spectra were determined with a Nexus470 FTIR 103 using a 4" pathlength cell (not shown) with KBr windows (not shown).

The chamber 101 comprised a transparent window 107 to allow visual access to the sample under test for viewing the smoke and measuring smoke parameters. A vent hood 104 collected fumes from the test and a vent 105 vented fumes outside of the building.

In a similar test of the smoke producing sample, a 50 $f^{t3}$ PVC and plastic wrapped chamber (not shown) was constructed. Two clear plastic windows 204 (FIG. 2*a*) on the chamber 200 (FIG. 2*a*) provided for optical measurements and visualization of the smoke production.

A series of experiments were completed in both the 1 $ft^3$ and 50 $ft^3$ chambers to test the limits of smoke production with increasing initiator concentration. Measurements of smoke production versus initiator concentration from 5 to 50 pph have been made in the 1 $ft^3$ chamber and from 5 to 25 pph in the 50 $ft^3$ chamber. For tests in both the 1 $ft^3$ and 50 $ft^3$ chambers optical transmission measurements ($I/I_0$) were made versus time using a 633 nm laser and Newport laser power meter. From these tests it was determined that increasing the initiator concentration to at least 25-30 pph gave a good smoke production reaction and that increasing to 50 pph would continue to produce more smoke. Tests were run to quantify the amount of material necessary to produced a dense enough smoke for obscuration. A series of tests using different sample weights with 25 pph starting material versus optical density were run in the 50 $ft^3$ chamber. The amount of material was increased from 5 to 25 grams of monomer (all with 25 pph of initiator); this corresponds to 0.1 to 0.5 grams of monomer per $ft^3$ of chamber volume.

Figure 2A:
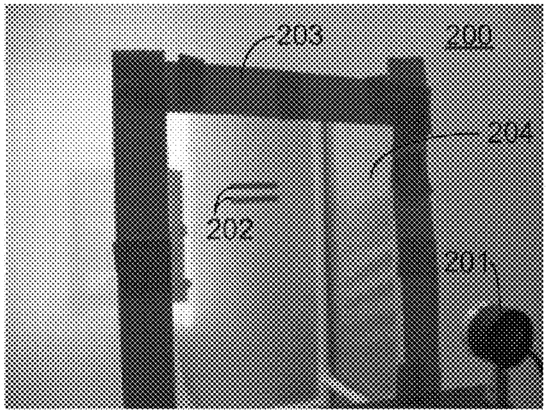
FIGS. 2*a*-2*f* show a series of photographic measurements showing the smoke density increase as increasing amounts of sample smoke producing material are activated.
Figure 2B:
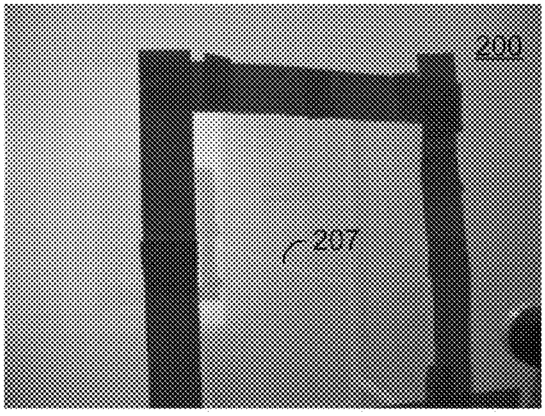

FIGS. 2*a*-2*f* show a series of photographic measurements showing the smoke density increase as increasing amounts of sample smoke producing material are activated. A laser power meter 201 measured optical transmission of smoke in the chamber 200. Tape 203 defined a rectangular transparent window 204. Two tape strips 202 were mounted horizontally on the opposite inside side wall of the chamber. As can be seen in FIG. 2*a*, which illustrates the chamber 200 before a smoke producing reaction is initiated, the tape strips 202 are clearly visible through the window 204. However, as smoke concentration increases, as shown in FIG. 2*b*, in which the smoke density is 0.10 grams monomer per cubic foot, the tape strips 202 become less visible. The beam 207 from the laser power meter 201 is clearly visible in FIG. 2*b*.

Figure 2C:
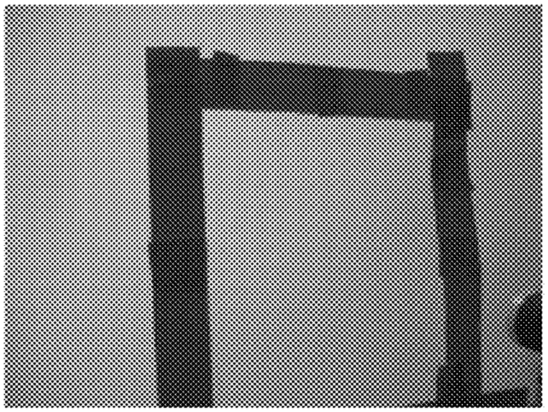
Figure 2D:
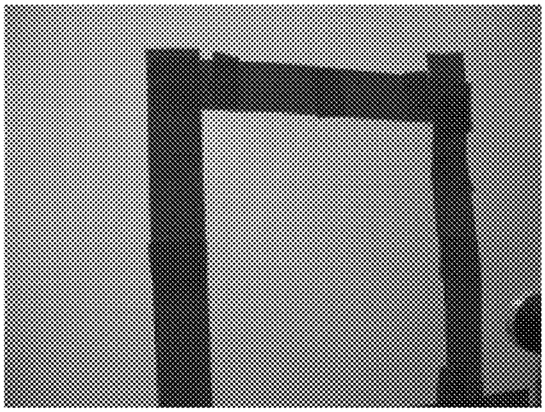
Figure 2E:
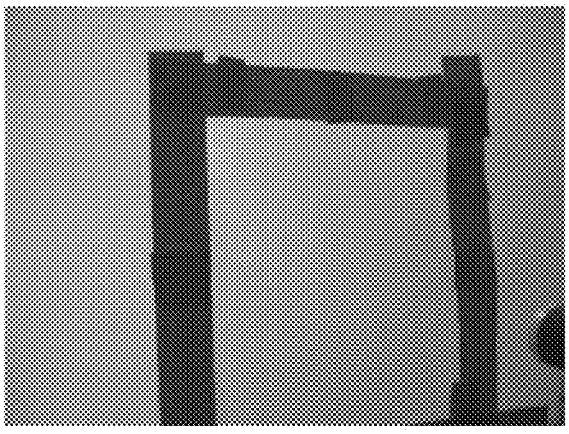
Figure 2F:
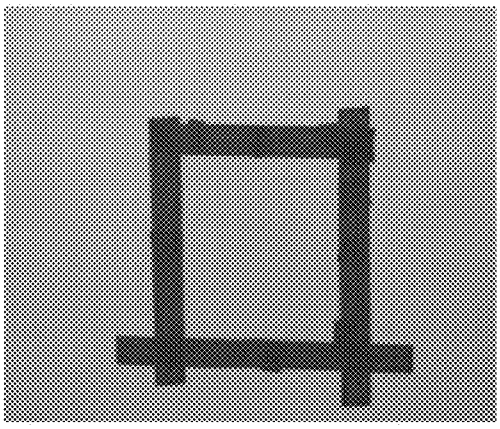

In FIG. 2*c*, which illustrates a smoke density of 0.15 grams monomer per cubic foot, the tape strips 202 are invisible. In FIG. 2*d*, the smoke density is 0.20 grams monomer per cubic foot. In FIG. 2*e*, the smoke density is 0.25 grams monomer per cubic foot. In FIG. 2*f*, the smoke density is 0.30 grams monomer per cubic foot.

It is notable that the testing illustrated in FIGS. 2*a*-2*f* was performed indoors in plastic containment chambers. This highlights the non-incendiary characteristic of the reaction. The smoke does have an odor to it so the chamber needs to be vented outside. However, an unpleasant odor could be advantageous in some situations where a “stink bomb” might be desired.

Figure 3:
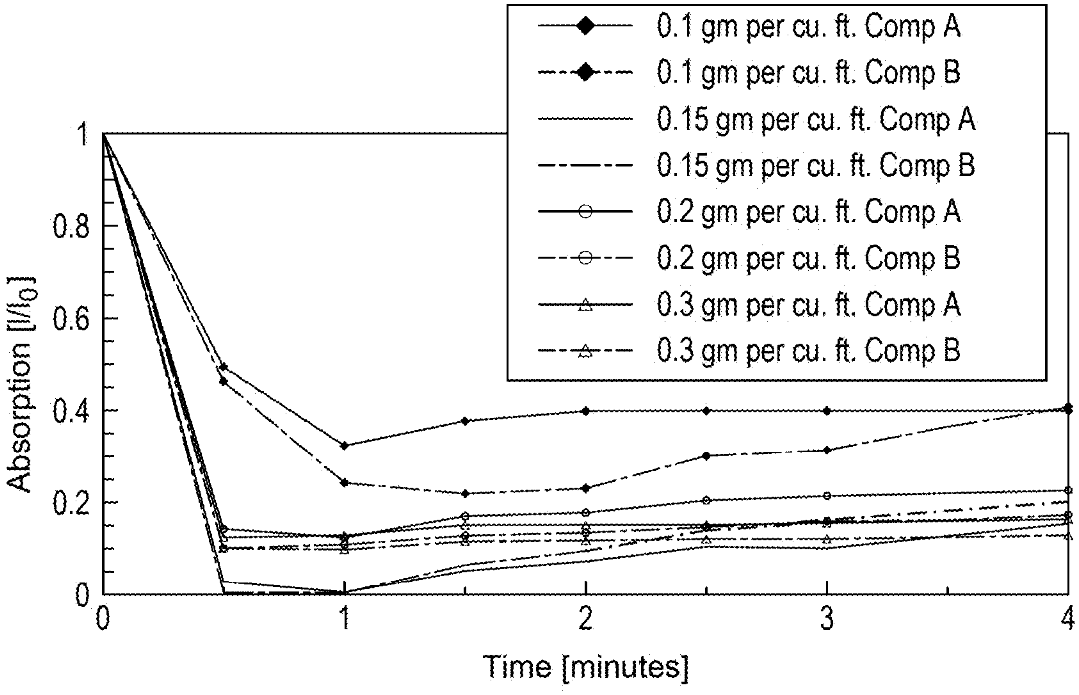
FIG. 3 is plot of the optical density versus time for a variety of smoke producing compositions under test.

FIG. 3 is a plot of the optical density versus time for the same mass of materials from testing performed in 50 ft3 chamber. This figure shows that after about 0.15 grams of starting monomer per cubic foot ($gm/ft^3$), the optical density drops below 0.1. Comparing the results of FIG. 2*c* with FIG. 3 at 0.15 $gm/ft^3$ the smoke density is almost sufficient to totally obscure the reference tapes 202 (FIG. 2*c*) on the opposite wall. As the sample mass increases up to 0.3 gcf the smoke density and its obscurant ability clearly increase.

The photographic series FIGS. 2*a*-2*f* illustrates a quirk of the laser beam visibility: with increasing smoke density, the laser beam 207 actually seems brighter and more visible. This result is also shown in the data of FIG. 3. The measured optical density for starting sample mass of greater than 0.15 gcf is actually greater than for 0.15 gcf itself, while it is clear from the photographs in FIG. 2*c*-2*f* that the smoke is denser. This higher measured optical density is likely due to a multiple scattering phenomena competing with the initial beam absorption/scattering. Note also from FIG. 3 that the duration of the smoke (at least in this controlled environment, i.e., in the absence of driving winds) is considerable.

Decomposition Products

The starting monomer and initiator in the exemplary testing was TMPTA and Luperox® 231. The expected decomposition products have been analyzed both through a literature review and via Gas Chromotograph-Mass Spectrometer (GC-MS) analysis of the smoke products. The literature review lists as the decomposition products:

a. 3,3,5-trimethylcyclohexane,
b. 2,4,4-trimethylcyclohexane,
c. Trimethylcyclopentane
d. t-butyl alcohol,
e. acetone,
f. methane, and
g. carbon dioxide.

Experimental GC-MS analysis essentially confirmed the literature results but showed only three components in the smoke:

a. 3,3,5-trimethylcyclohexane,
b. 2,4,4-trimethylcyclohexane, and
c. t-butyl alcohol.

Neither acetone nor trimethycyclopentane were detected. The molecular weights and melting and boiling points of some of the decomposition components are listed in Table 2 below. Acetone and Tert-butyl alcohol are gases room temperatures and the trimethylcyclohexane is liquid droplets at room temperature.

TABLE 2

| Molecular weights and melting and boiling points of Luperox ® 231 decomposition products | | | |
|---|---|---|---|
| Decomposition Product Vapor Species | Molecular Weight [g/mole] | Melting Point [° C.] | Boiling Point [° C.] |
| 1,3,5-trimethylcyclohexane | 126.24 | −49.7 | 138.5 |
| Acetone | 58.08 | −95 | 56.2 |
| Tert-butyl alcohol | 74.12 | 25.2 | 82.2 |

Figure 4A:
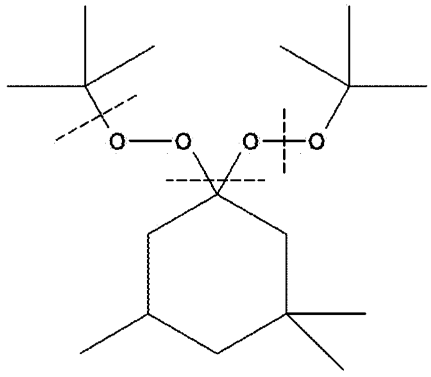
FIG. 4*a* is a schematic of a hypothetical mechanism of the decomposition pathway of the Luperox® 231.
Figure 4B:
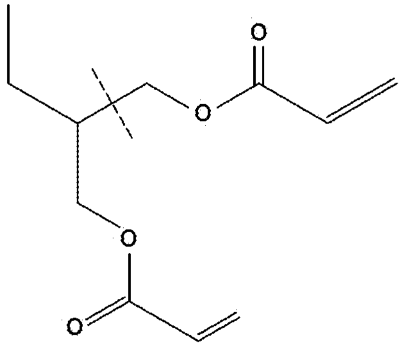
FIG. 4*b* is a schematic of a hypothetical mechanism of the decomposition pathway of the mono- and di-function monomer impurities in the commercial grade TMPTA.

FIG. 4*a* is a schematic of the decomposition pathway of the Luperox® 231 and FIG. 4*b* is a schematic of the decomposition pathway of the mono- and di-function monomer impurities in the commercial grade TMPTA. In this schematic, dotted lines are cleavage.

From the GC-MS analysis of the smoke produced, the reaction products are trimethylcyclohexane and t-butyl alcohol. The reaction products of the monomer decomposition are not seen in the smoke but may affect its infrared absorption properties.

Total Sample Mass Loss During Smoke Production

A series of tests were performed to measure the mass loss of the sample smoke generation compound versus the amount of initiator used in the compound. These tests were performed to confirm that the majority of the initiator was decomposing, and this expectation was confirmed. For the higher initiator concentrations and for thin (<⅛") sample thickness, there was more mass loss than just the initiator itself. The significance of sample thickness is discussed further below.

A series of tests was also performed to determine the mass loss over a wider initiator concentration range, and the initiator concentration was varied from 1 pph to 30 pph. The fumed silica (thickening agent) content was held constant at 10 pph. The starting TMPTA monomer was 2 grams and the mass of the initiator was varied from 0.02 to 0.60 grams. Two to three samples were run for each mixture composition. The results of these tests are presented in Table 3 below.

TABLE 3

| Percent mass loss of monomer-initiator-filler mixtures versus the initial initiator concentration. | | | | | |
|---|---|---|---|---|---|
| | Initiator Concentration [parts per hundred] | | | | |
| | 1 | 5 | 10 | 20 | 30 |
| Percent mass loss (number of samples) | 0.5-1 (2) | 4.0-5.2 (3) | 9.8-13.4 (3) | 22-32 (3) | 33-49 (2) |

As can be seen from Table 3, from about 1 to 5 pph of initiator, the mass loss was approximately proportional to the amount of initiator added. At higher initiator concentrations (greater than 10 pph) the total mass loss was greater than the initiator mass. The additional mass loss—resulting in more smoke—is considered to be due to a decomposition of mono-functional, and di-functional "impurities" that are present in the commercial grade TMPTA. The additional mass loss could be due to a decomposition of the tri-functional TMPTA itself, but this is considered to be unlikely.

Figure 5:
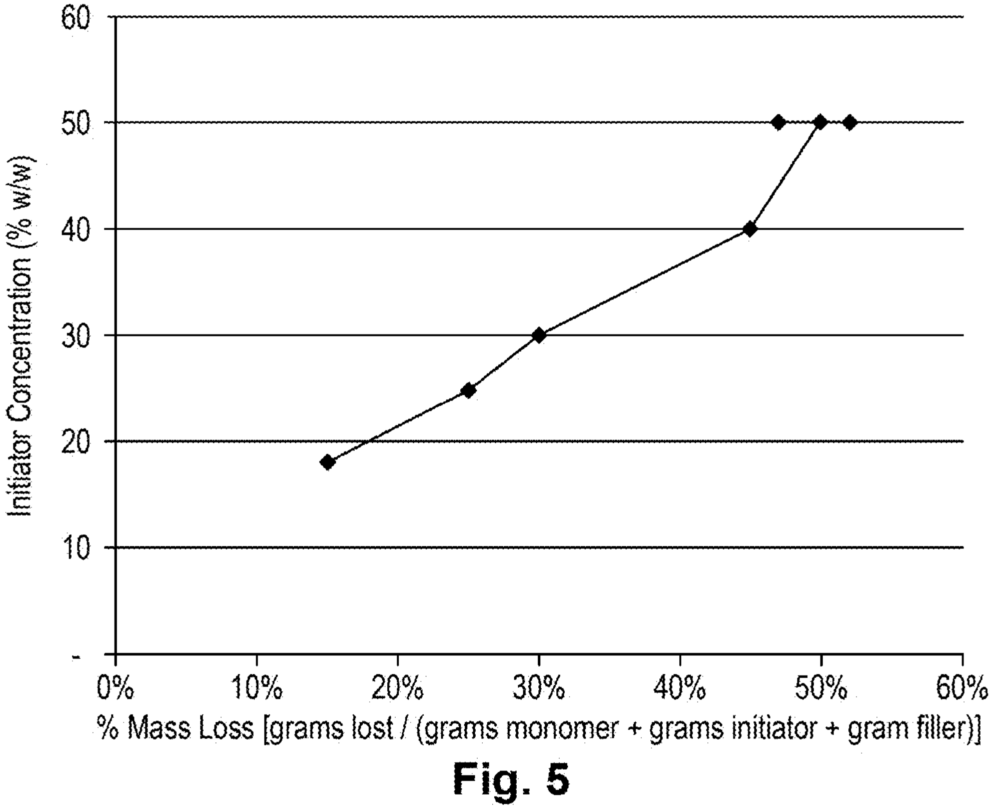
FIG. 5 illustrates the results of an additional series of tests run with concentrations approaching 50 pph.

FIG. 5 illustrates the results of an additional series of tests run with concentrations approaching 50 pph. Note that it is unclear whether that the mass loss rate is decreasing at the 50 pph (50%) point. This indicates that it is desirable to perform additional tests with initiator concentrations greater than 50 pph.

The internal temperature of 5 gram samples of the mixed compound was measured in order to better understand the safety, and non-incendiary, characteristics of the frontal polymerization reaction. In initiator concentrations of less than 5 pph, the internal sample temperature was 100-200° C. At initiator concentrations from about 15 to 30 pph, the internal temperature increased to 300-350° C. This temperature is likely sufficient to lead to some decomposition of the monomer itself, which may be helped by the appreciable excess of initiator.

Effect of Sample Layer Thickness and Geometry on Smoke Production

A series of tests was performed to determine the effect of aspect ratio (width v. length at fixed heights) of the sample versus the amount of smoke produced. These tests were conducted under three testing/operating scenarios, 1) front and rear initiation of the reaction, 2) cylindrical samples of varying aspect ratio, initiated from the top "free" surface, and 3) rectangular samples of varying aspect ratios. Test geometries 1) and 2) were conducted in the one $ft^3$ test chamber and the third series of tests were conducted in the 50 $ft^3$ chamber. The sample smoke producing compound was 10 pph Luperox® 231 and 10 pph fumed silica filler.

Tests of Front Versus Rear Reaction

Figure 6A:
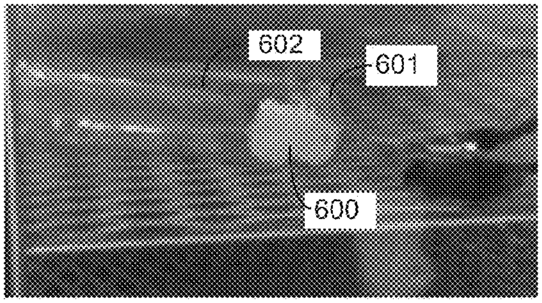
FIGS. 6*a*-6*c* illustrate the tests performed to analyze initiation of a smoke producing reaction to measure the amount of smoke produced when the reaction was initiated from the front of a smoke producing sample contained in a glass vial.
Figure 6B:
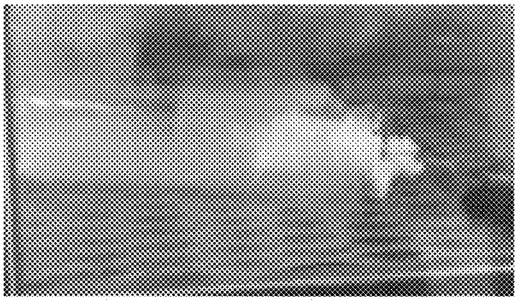
Figure 6C:
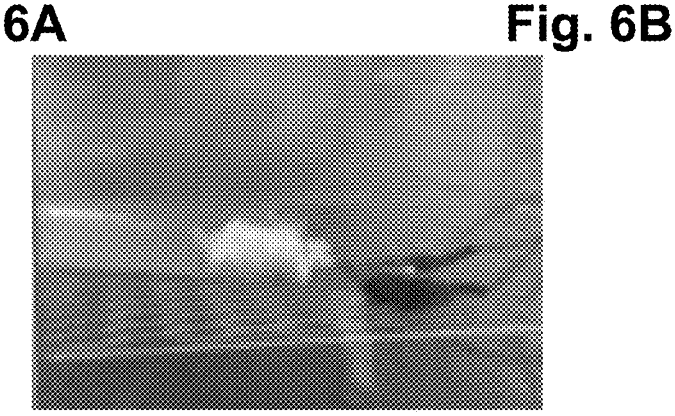

FIGS. 6*a*-6*c* illustrate the tests performed to analyze initiation of a smoke producing reaction to measure the amount of smoke produced when the reaction was initiated from the front, expanding portion, of the sample contained in a glass vial. In FIG. 6*a*, the sample 600 is disposed near an open front end 601 of a glass vial 602. In FIG. 6*b*, the sample 600 has just been ignited. FIG. 6*c* is a wider view of the sample 600 after the smoke has expanded. The smoke was close to neutrally buoyant and filled the test chamber in an amount that would be expected, given the size of the sample.

Figure 7A:
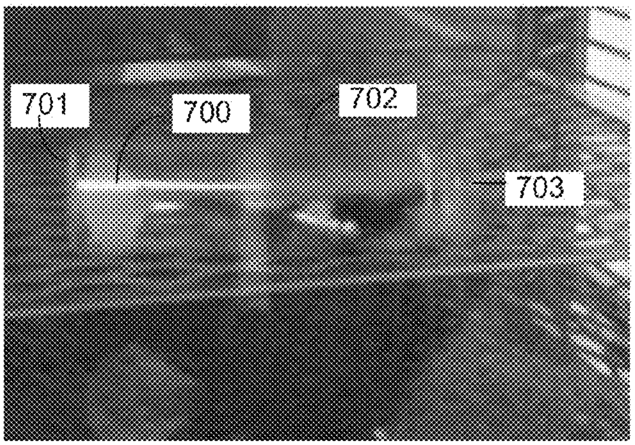
FIGS. 7*a*-7*c* illustrate the tests performed to analyze initiation of a smoke producing reaction.
Figure 7B:
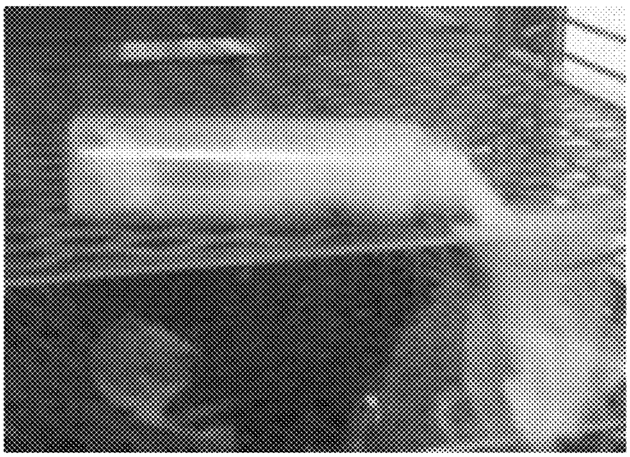
Figure 7C:
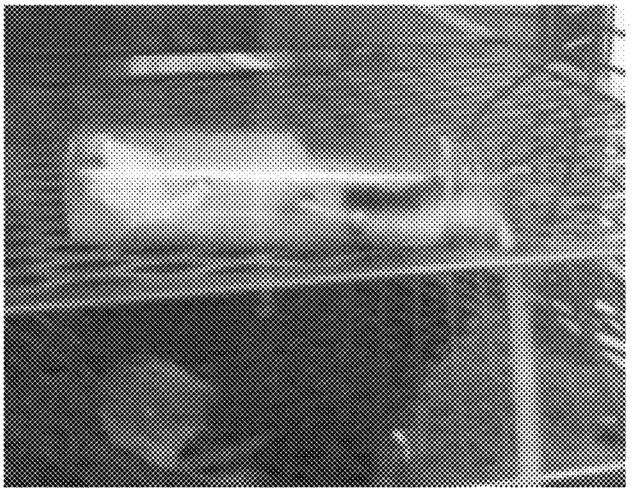

FIGS. 7*a*-7*c* illustrate the tests performed to analyze initiation of a smoke producing reaction to measure the amount of smoke produced when the reaction is initiated from a sample disposed in the rear, constrained, portion of a glass vial. In FIG. 7*a*, the sample 700 is disposed near the rear end 701 of a glass vial 702. In this series of tests, as shown in FIGS. 7*b* and 7*c*, any hot smoke vapors have to travel through the unreacted portion of the sample before reaching the open end 703 of the vial 702. The resultant smoke was denser than the surrounding air and tended to sink to the bottom of the test chamber. In both of the tests illustrated in FIGS. 6 and 7, the frontal polymerization reaction proceeded to completion.

Tests of Cylindrical Samples of Varying Aspect Ratios

Figure 8:
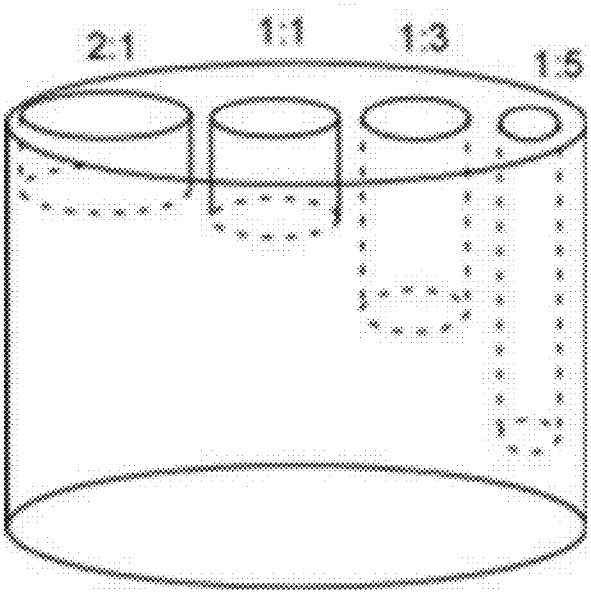
FIG. 8 illustrates a plurality of cylindrical shapes tested in a series of trails of the smoke producing composition.

The second series of trials tested a constant volume of material in three cylinder shapes with bores of different aspect ratios, 2:1, 1:1, 1:3, and 1:5, as illustrated in FIG. 8. The cylinder bores were generated by drilling holes in a Delrin puck. A syringe was used to place the samples in the bore holes. These tests showed that the 2:1 aspect ratio sample had the most smoke production; the 1:3 and 1:5 aspect ratio tests produced a minor amount of smoke. The 2:1 aspect ratio test produced a typical amount of smoke. The test results are reported in Table 4 below. In each of these tests, the reaction was initiated at the top of the sample with enclosed sides and bottom. The conclusion from these tests is that a low aspect ratio of height to diameter is desirable.

TABLE 4

| Optical transmittance of smoke produced for various aspect ratio cylindrical samples | | |
|---|---|---|
| Sample Aspect Ratio [diameter to height] | Sample Diameter [inches] | Optical Transmittance [I/I0] |
| 2:1 | 1 | 0.20 |
| 1:1 | ⅝ | 0.8 |
| 1:3 | ½ | 0.97 |
| 1:5 | ¼ | 1.0-no signal loss |

Tests of Rectangular Samples of Varying Aspect Ratios

Figure 9:
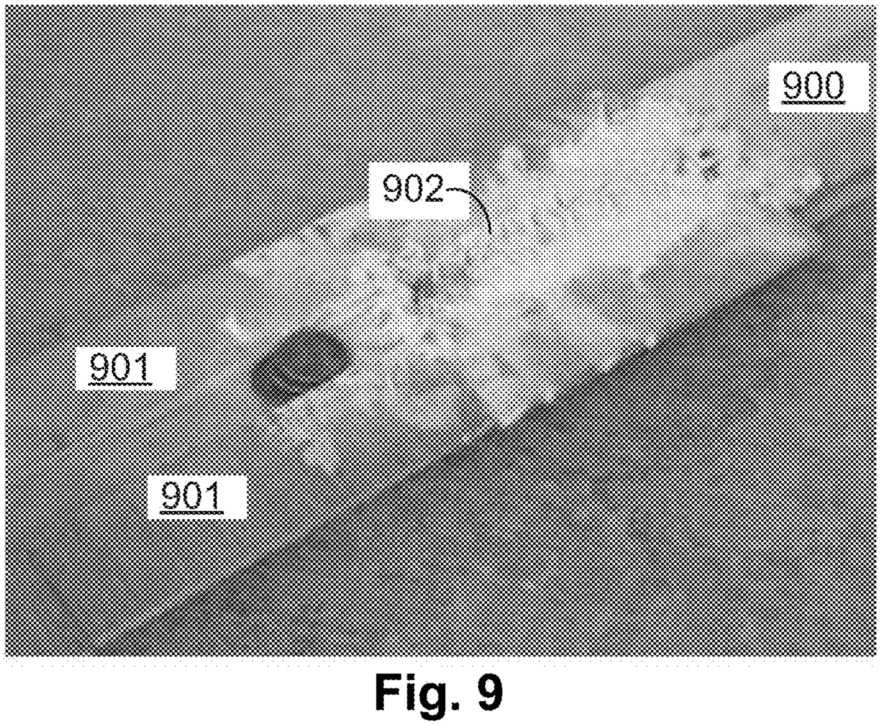
FIG. 9 is a photograph of a test setup from a series of tests of the smoke producing composition spread out on a section of lumber.

FIG. 9 is a photograph of a test setup from the final series of tests, which were conducted with 10 gram samples (20 pph initiator, 10 pph silica), spread out on a section of lumber 900. Selected thickness lumber guide rails 901 were spaced about one inch apart, the guide rails were varied from 3/16 inches in height, to ¼" in height to ½" in height, and the sample 902 (shown after the reaction) was spread out to roughly 1.5 to 4 inches long between the guide rails. Note that the in FIG. 9 lumber shows no signs of combustion and in spite of the fact that it has been used for several dozen tests. The measured optical density values are given in Table 5 below. These results confirm that the layer thickness play a critical role in the efficiency of smoke produced.

TABLE 5

| Optical transmittance measurements versus aspect ratio and sample thickness for fixed mass samples. | | | |
|---|---|---|---|
| Sample Aspect Ratio [height to length] | Sample Thickness [inches] | Sample Length [inches] | Optical Transmittance [I/I0] |
| 1:20 | 3/16 | ~4 | 0.10 |
| 1:12 | ¼ | ~3 | 0.25 |
| 1:3 | ½ | ~1.5 | .98-no signal loss |

Test with Monomers and Initiators Other than TMPTA and Luperox® 231

A series of tests were conducted with TMPTA and initiators other than Luperox® 231 and tests of monomers other than TMPTA to confirm that the smoke production was due to the decomposition of the Luperox® 231 and to confirm the effectiveness of TMPTA as the monomer. These tests were only run for qualitative, rather than quantitative smoke production assessment. The mixture composition was 10 pph initiator and 10 pph fumed silica. Table 6 shows the results of these tests.

TABLE 6

| Monomer-Initiator combinations tested for their qualitative smoke production ability. | | |
|---|---|---|
| | Initiators | |
| Monomers | Luperox ® 231 | t-butyl peroxybenzoate |
| TMPTA (Trimethylolpropane triacrylate) | Good smoke-Control sample | Similar to Control |
| TMPTA + dibutyl phthalate | Good or better smoke-smoke sinks | No Test |
| PETA (Petaerythritol triacrylate) | Poor smoke | Poor smoke |
| DTMPTA (Di(trimethylolpropane) triacrylate) | Poor or no smoke | No smoke |

TABLE 6-continued

| Monomer-Initiator combinations tested for their qualitative smoke production ability. | | |
|---|---|---|
| | Initiators | |
| Monomers | Luperox ® 231 | t-butyl peroxybenzoate |

The results in this table highlight the fact that the Luperox ® 231/TMPTA initiator/monomer combination is rather unique in its ability to produce large volumes of smoke. The t-butyl peroxybenzoate initiator did produce good quality of smoke. However, one of its reaction products would be benzoic acid. Thus, a smoke from this initiator would have a much higher toxicity than the methylcyclohexanes from Luperox ® 231. The TMPTA + dibutyl phthalate mixture did produce a good quality, albeit sinking, smoke.

Visible Optical Signatures

Figure 10:
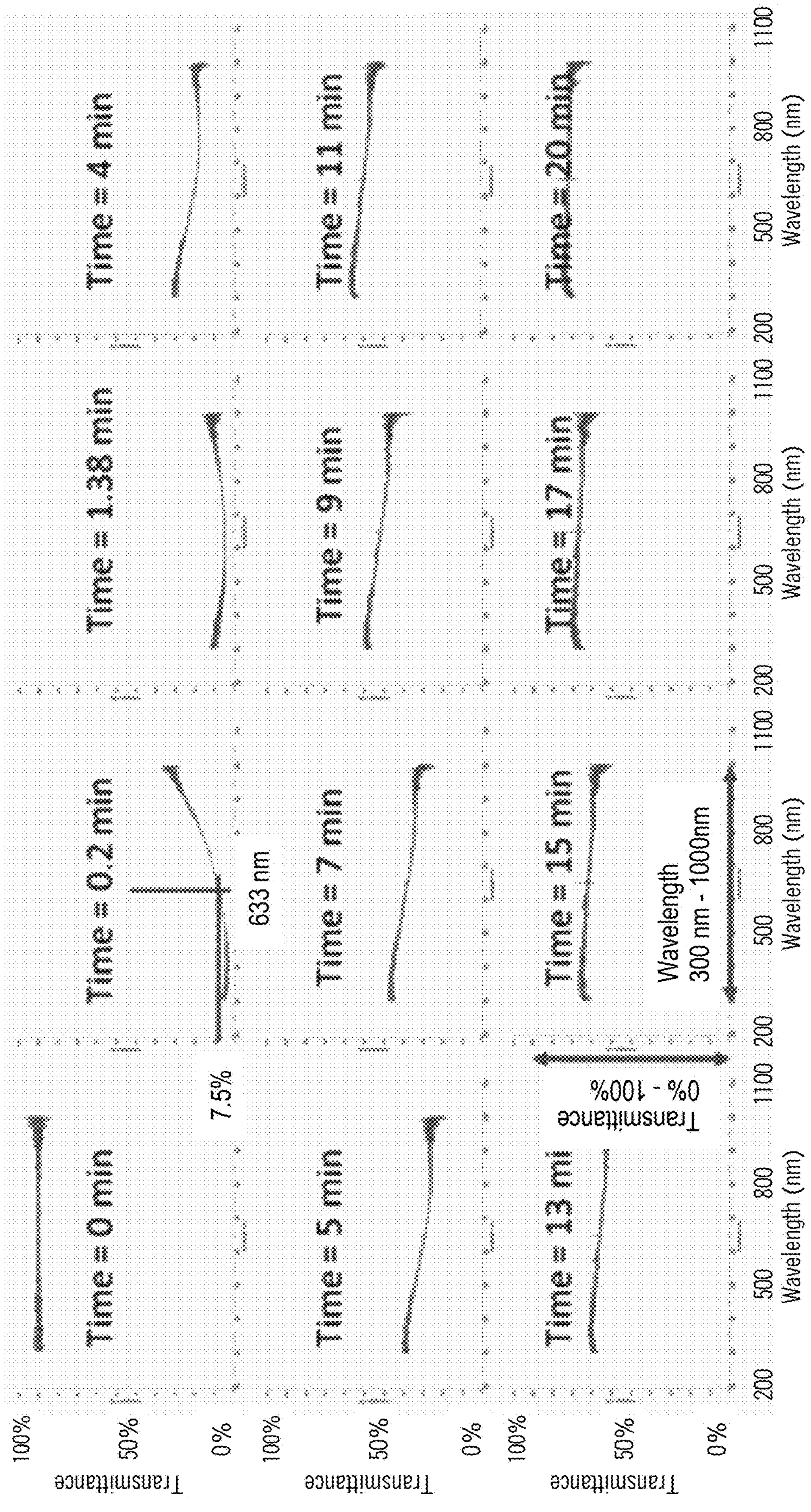
FIG. 10 illustrates the visible absorption spectrum of the smoke produced from the TMPTA-Luperox 231 reaction from the start of the reaction to about 20 minutes after is shown.

FIG. 10 illustrates the visible absorption spectrum of the smoke produced from the TMPTA-Luperox 231 reaction from the start of the reaction to about 20 minutes after is shown. The data was taken using the one ft3 chamber that was connected to the Ocean Optics spectrometer through flow-ports installed in the back of the chamber. This figure shows that the smoke produced has a uniform absorption across the (entire) visible spectrum from 300-1000 nm. Thus, it evenly scatters all the visible wavelengths. It can also be seen in the figure that the smoke has a persistence of at least 5 minutes. From this data and from other tests this indicates that the particle sizes are in a range where there is not rapid sedimentation of the particles or droplets.

Infrared Optical Signatures

Figure 11:
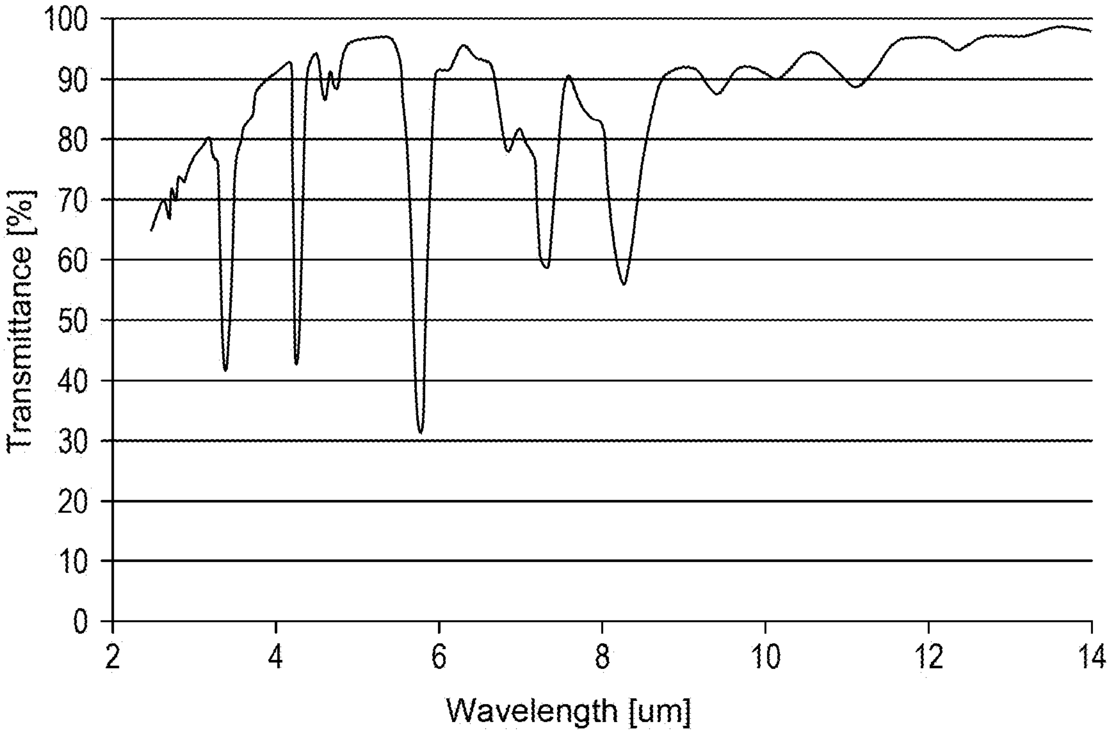
FIG. 11 illustrates the infrared absorption spectrum of the smoke produced from the TMPTA-Luperox 231 reaction from the start of the reaction to about 9 minutes after the reaction.

FIG. 11 illustrates the infrared absorption spectrum of the smoke produced from the TMPTA-Luperox 231 reaction from the start of the reaction to about 9 minutes after the reaction. The data was taken using the 1 $ft^3$ chamber that was connected to the Nexus 470 FTIR system through flow-ports installed in the back of the chamber. The infrared cell has KBr windows. The infrared spectrum has unique peaks associated with the trimethylcyclohexane, t-butyl alcohol, and acetone produced in the reaction. The infrared peak from a human body is centered around 101 ▯m; indicating that the current version of this smoke is not an infrared obscurant for humans. The absorption peaks at approximately 6, 7 and 8 ▯m indicate that the smoke has obscurant properties for 225, 150, and 100° C. bodies. No efforts were made during the Phase I research to modify the reaction products to make the smoke obscure humans.

Toxicity of Decomposition Products

The toxicity of the decomposition products has been analyzed from the MSDS data that is available for the initiator decomposition products: trimethylcyclohexane, tert-butyl alcohol, and acetone. Values for the known decomposition products of our formulation and current inventory grenades are given in Table 7 below. While excessive exposure to acetone and ter-tbutyl alcohol should be avoided, these compounds are the primary component of many household products such as nail polish remover. Table 7 below shows that the decomposition products of the smoke producing formulation disclosed herein are substantially less toxic or reactive than presently used compounds. (Hexachloroethane and phosphoric acid are included as reference materials.)

TABLE 7

Toxicity and workplace exposure data for Luperox® 231 decomposition products.

| | LD50 [mg/kg] | Exposure limit [(mg/kg)/time-hrs] | notes |
|---|---|---|---|
| trimethylcyclohexanes | No data | No data TWA 2000 mg/$m^3$ | Chronic effect on humans-toxic to lungs |
| methylcyclohexane | 2,250-oral | 7613 vapor-4 hours | Chronic effect on humans-toxic to lungs |
| tert-butyl alcohol | 2,743-oral | 10,000 vapor-4 hours | may cause reproductive system damage |
| acetone | 3000-oral | 44,000 vapor-4 hours | may cause CNS damage |
| hexachloroethane (M8 HC) | 4,900-oral | No data, but known respiratory irritant TWA-10 mg/m3 | Confirmed animal carcinogen, very toxic to aquatic life-long lasting |
| Terephthalic acid (M83TA) | 3200 | TWA-10 mg/$m^3$ | Chronic toxicity to multiple organ systems |
| phosphoric acid | 1550-oral | 850 vapor - 1 hour | TLV-1 mg/$m^3$ |

LD50 = Median Lethal Dose
TWA = Time Weighted Average
TLV = Threshold Limit Value Questions have been raised as to whether adding oxiders to the mix would it speed up the reaction and make smoke faster. The composition is not incendiary, and adding (inorganic) oxidizers to the mix may cause it to start a fire, which would be undesirable. Therefore, the composition avoids inorganic oxidizers. The smoke in the composition is produced from the decomposition of the initiator in the composition, which can be thought of as an/the oxidizer. The composition differs from currently known formulations in that it is this "oxidizer" that makes the smoke. Adding an inorganic oxidizer would likely cause the smoke production to decrease.

The desired smoke production requires approximately 0.020 grams of material per cubic foot of obscured volume when viewed through a 10 m thick smoke screen. For a 5 m thick smoke screen 0.04 grams/cu. ft. of material are required. The obscurant factor is constant across the visible spectrum, and has infrared absorption in specific wavelength ranges. Assuming ideal and complete reaction efficiency, for a 300 $m^3$ (3 m×10 m×10 m or 10,600 $ft^3$) obscured volume, approximately 200 $cm^3$ of material is projected to be required, representing a device approximately 4 inch in height and 2 inches diameter; without casing, fuse or ignition source. Analysis of the mechanism of smoke production indicates a strong potential that a smoke could be produced with 0.010-0.015 grams of material per cubic foot of required coverage. The casing and fusing requirements will result in a final device size of generally 5 inches in height and about 3 inches diameter; which represents devices currently in the inventory.

It is unlikely that the local oxygen concentration has any effect on the amount of smoke produced. Based upon the decomposition mechanism of the Luperox® 231, oxygen is not required. It is currently unknown whether extra mass loss from the mono- or di-functional monomers requires oxygen or not.

Figure 12:
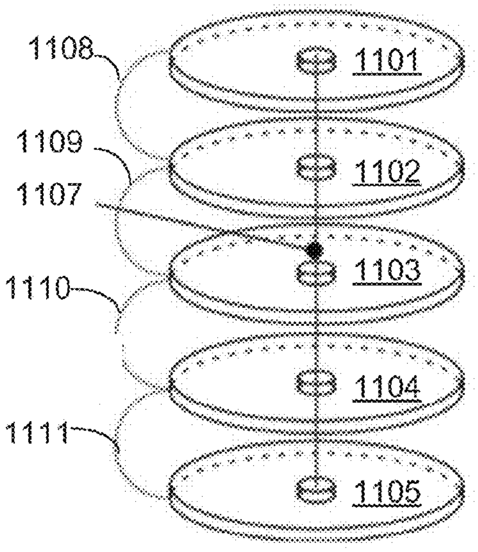
FIG. 12 depicts a stacked disked embodiment of a smoke generating device.

FIG. 12 depicts an embodiment of a smoke generating device 1100 using the compound disclosed herein. In this "stacked disk arrangement," the smoke generating compound (not shown) is applied to disks 1101, 1102, 1103, 1104 and 1105 stacked atop one another. Although five (5) disks 1101-1105 are shown in FIG. 11, this number of disks is illustrated for explanatory purposes; a smoke generating device 1100 may comprise 10-30 stacked disks, or more or fewer, as desired.

In this embodiment, each disk 1101-1105 is formed from non-woven fiber, such as a plastic fiber similar to Scotch Brite® pads or a plastic Brillo® pad, or fiberglass. The disks 1101-1105 may also be formed from other materials with a high surface area for maximizing the composition's exposure to oxygen during the smoke-producing reaction.

An ignition wire 1106 extends through openings 1107 in the disks 1101-1105 for initiating the reaction. In other embodiments, the ignition wire 1106 may be "woven" into the fiber comprising the disk.

Wires 1108, 1109, 1110, and 1111 extend between adjacent disks. In this regard, wire 1108 extends between disk 1101 and disk 1102; wire 1109 extends between disk 1102 and disk 1103; wire 1110 extends between disk 1103 and disk 1104; wire 1111 extends between disk 1104 and disk 1105.

In some embodiments, insulators (not shown) are disposed between adjacent disks to isolate each disk from the remaining disks, to prevent the disks from sticking together.

Figure 13:
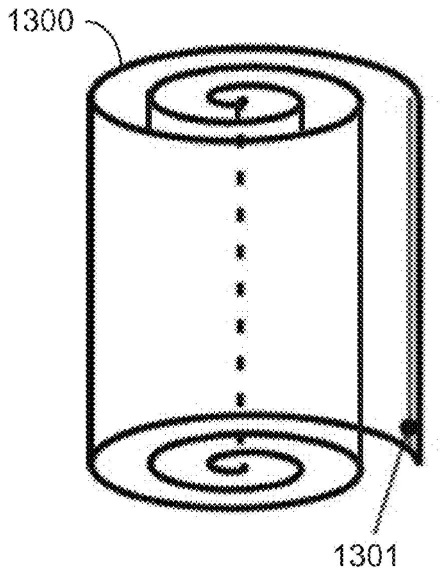
FIG. 13 depicts an embodiment of a smoke producing device comprising a substrate formed from a single sheet of material, rolled into a spiral shape.

FIG. 13 depicts an embodiment of a smoke producing device comprising a substrate 1300 formed from a single sheet of material, rolled into a spiral shape as shown. The substrate 1300 may be formed from the materials discussed above with respect to FIG. 12. An ignition line 1301 extends through the substrate 1300.

Figure 14:
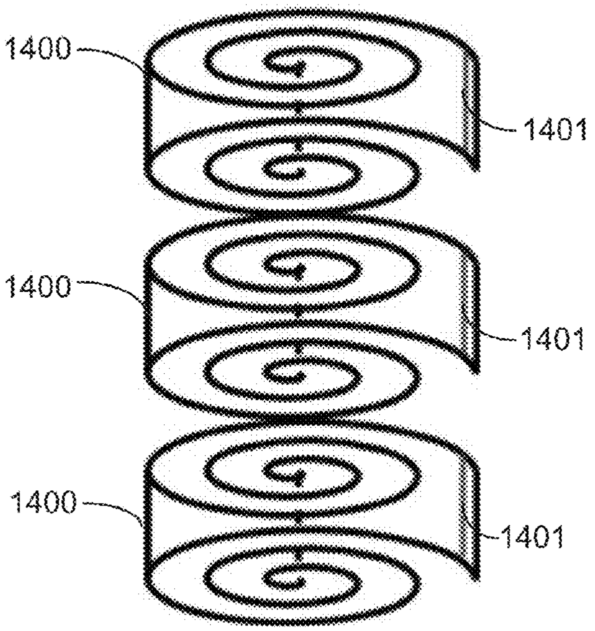
FIG. 14 depicts a "stacked spiral" arrangement in which a plurality of spiral substrates are stacked atop one another.

FIG. 14 depicts a "stacked spiral" arrangement in which a plurality of spiral substrates 1400 like those discussed above with respect to FIG. 13 are stacked atop one another. Each substrate comprises an ignition line 1401.

Figure 15A:
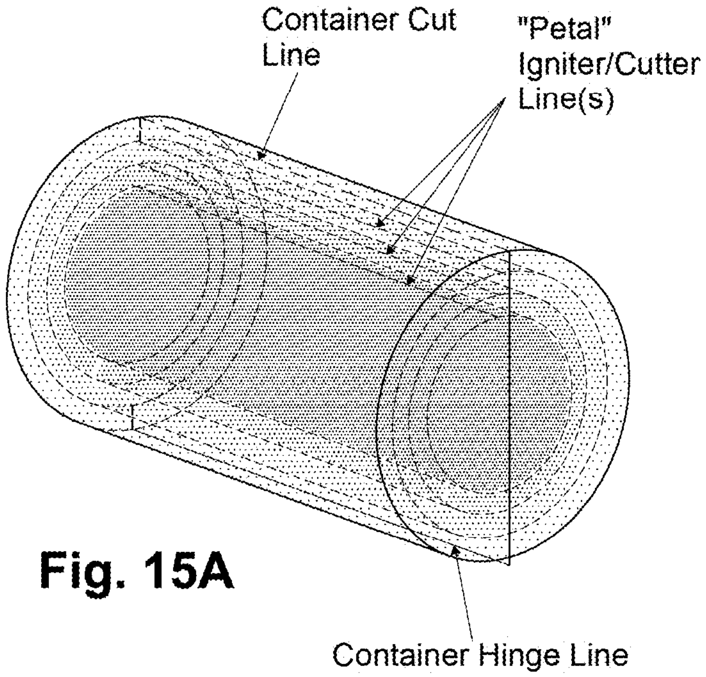
FIGS. 15*a*, 15*b* and 15*c* depict an embodiment of a smoke producing device in which a plurality of cylindrical petals are arranged "concentrically" inside a cylindrical container that is hinged on one side.
Figure 15B:
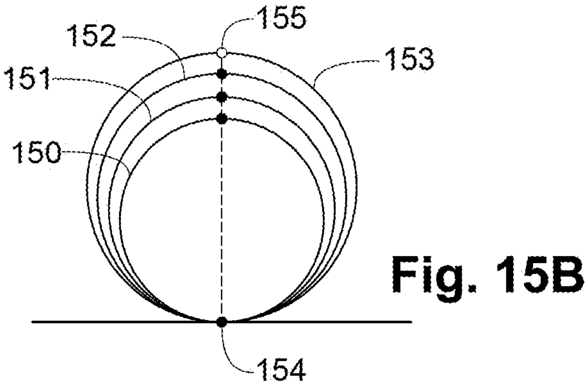
Figure 15C:
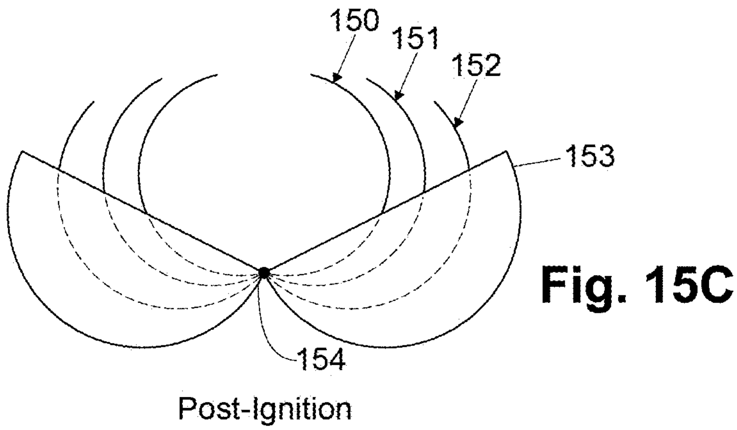

FIGS. 15*a*, 15*b* and 15*c* depict an embodiment of a smoke producing device in which a plurality of cylindrical petals 150, 151 and 152 nested inside a cylindrical container 153 that is hinged on one side via a hinge 154. FIGS. 15*a* and 15*b* depict the container 153 before the smoke producing ignition is initiated, and FIG. 15*c* depicts the container 153 after the ignition has begun. Although three petals 150, 151, and 152 are depicted in the illustrated embodiment, more or fewer petals are employed in other embodiments.

The ignition sequence causes the container 153 to be split so that it opens up along a hinge line 155 of the container 153. The concentrically arranged petals 150, 151 and 152 are ignited and split along one side so that they "open up" like a blooming flower. Each of the petals 150, 151 and 152 may be formed from the materials discussed with respect to FIG. 12 above.

Tests of Capsaicinoid Smoke Generation

A first test was performed by adding commercially available oleoresin *Capsicum* (ethanol extract from *Capsicum* fruit) to a non-pyrotechnic smoke composition comprising 10% w/w monomer, 10% w/w fumed silica filler, and 80% w/w initiator. The oleoresin *Capsicum* was added to the non-pyrotechnic smoke composition at a ratio of 1 part oleoresin *Capsicum* to 10 parts smoke composition by weight. A frontal polymerization reaction was initiated in 10 g of the mixture placed in an enclosed shipping container 8 feet (2.44 m) by 10 feet (3.05 m) by 40 feet (12.19 m) (90.7 $m^3$). Smoke production was observed to be very slow. When two human test subjects approached the shipping container after the completion of smoke production, they were immediately repelled upon contact with the smoke. The subjects coughed and reported irritation of the sinuses and lungs. The test was repeated using a mixture at a ratio of 1 part oleoresin *Capsicum* to 20 parts smoke composition by weight. Smoke production was not slowed. However, the test subjects were able to tolerate contact with the smoke for several minutes.

A second test was performed using crystalized capsaicin in place of *Capsicum* oleoresin. Capsaicin was added to the same smoke composition at a ratio of 1 part capsaicin to 10 parts smoke composition by weight. A frontal polymerization reaction was initiated in 10 g of the mixture placed in an enclosed warehouse 25 feet (7.62 m) by 25 feet (7.62 m) by 25 feet (7.62 m) (442.5 $m^3$). The rate of smoke production did not appear to be affected by the addition of the capsaicin. When two human test subjects approached the warehouse after the completion of smoke production, they were immediately repelled upon contact with the smoke. The subjects coughed severely and reported burning irritation of the eyes and nasal passages. The test was repeated using a mixture at a ratio of 1 part capsaicin to 20 parts smoke composition by weight with similar results.

CONCLUSIONS

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

The following is claimed:

1. A method of generating smoke non-pyrotechnically, the method comprising: (a) initiating a frontal reaction in a composition comprising an initiator compound in an amount sufficient to initiate and propagate the frontal reaction; and a filler agent in an amount sufficient to permit the frontal reaction to propagate once initiated; and (b) generating smoke that contains a reaction product of the initiator compound.

2. The method of claim 1, wherein the composition comprises a monomer compound that polymerizes upon initiation by the initiator compound, wherein the initiator compound is present at no less than 10 pph relative to the monomer.

3. The method of claim 1, wherein the composition contains no significant concentration of a monomer compound that polymerizes upon initiation by the initiator compound.

4. The method of claim 1, wherein the initiator compound is selected from: 1,1-bis(tert-butylperoxy)-3,3,5-trimethylcyclohexane, t-butyl peroxybenzoate, tert-butyl hydroperoxide, cyclohexyl hydroperoxide, and a combination of two or more of the foregoing.

5. The method of claim 1, wherein the initiator compound is t-butyl peroxybenzoate.

6. The method of claim 1, comprising a second initiator compound.

7. The method of claim 1, wherein the initiator compound is t-butyl peroxybenzoate; and comprising a second initiator compound.

8. The method of claim 1, wherein the initiator compound is t-butyl peroxybenzoate; and comprising a second initiator compound.

9. The method of claim 1, wherein the composition comprises an ester of vanillamine having a hydrocarbon tail at least 5 carbons in length.

10. The method of claim 1, wherein the composition comprises nonivamide.

11. The method of claim 1, wherein the composition comprises capsaicin.

12. The method of claim 1, wherein the composition comprises a capsaicinoid compound in an amount effective to produce an organoleptic effect in the smoke.

13. The method of claim 1, wherein smoke comprises a reaction product of the initiator compound.

* * * * *